US011000264B2

(12) United States Patent
Gunee et al.

(10) Patent No.: US 11,000,264 B2
(45) Date of Patent: May 11, 2021

(54) USER INTERFACE FOR A BIOPSY UNIT

(71) Applicant: KONINKLIJKE PHILIPS N.V., Eindhoven (NL)

(72) Inventors: Anders Rickard Gunee, Ronninge (SE); Per Mattias Myrman, Tyreso (SE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 1166 days.

(21) Appl. No.: 14/904,128

(22) PCT Filed: Jun. 30, 2014

(86) PCT No.: PCT/IB2014/062732
§ 371 (c)(1),
(2) Date: Jan. 11, 2016

(87) PCT Pub. No.: WO2015/008182
PCT Pub. Date: Jan. 22, 2015

(65) Prior Publication Data

US 2016/0128787 A1 May 12, 2016

(30) Foreign Application Priority Data

Jul. 19, 2013 (EP) .................................... 13306039

(51) Int. Cl.
*A61B 34/00* (2016.01)
*A61B 90/11* (2016.01)
(Continued)

(52) U.S. Cl.
CPC .......... *A61B 10/0041* (2013.01); *A61B 6/502* (2013.01); *A61B 10/0233* (2013.01);
(Continued)

(58) Field of Classification Search
None
See application file for complete search history.

(56) References Cited

U.S. PATENT DOCUMENTS 5,078,142 A 1/1992 Siczek
5,386,447 A 1/1995 Siczek
(Continued)

FOREIGN PATENT DOCUMENTS

CN 2065893 U 11/1990
CN 1064609 A 9/1992
(Continued)

*Primary Examiner* — Oommen Jacob
*Assistant Examiner* — Shahdeep Mohammed
(74) *Attorney, Agent, or Firm* — Larry Liberchuk

(57) ABSTRACT

The present invention relates to operating a biopsy unit. In order to provide an enhanced and facilitated way of controlling a biopsy unit, a control device (10) for controlling a biopsy unit is provided that comprises a support structure (12) with a housing (14), and a user interface unit (16) with a plurality of control elements (18). The control elements are configured to control the movement of a biopsy needle device along at least three moving direction lines. At least two of the moving direction lines are aligned to axes of a Cartesian coordinate system (20) and one moving direction line is aligned to a needle axis direction (22) of an elongated needle device of the biopsy unit, the needle axis direction being inclined to at least one of the axes of the Cartesian coordinate system. For each moving direction line, the housing is provided with a surface portion (24, 26, 28) that is aligned with a respective one of the moving direction lines. The control element for each moving direction line is arranged on the housing on a respective one of the surface portions; the control element for the movement along the needle axis direction being provided on an inclined surface portion (28) that is aligned with the inclined needle axis direction.

12 Claims, 3 Drawing Sheets

10 16 18 26 14 24 12 28 34 32 Z 23 22 20 X Z Y

(51) Int. Cl.

| | |
|---|---|
| ***A61B 10/02*** | (2006.01) |
| ***A61B 6/00*** | (2006.01) |
| ***A61B 10/00*** | (2006.01) |
| *A61B 17/34* | (2006.01) |

(52) U.S. Cl.
CPC .............. *A61B 34/25* (2016.02); *A61B 90/11* (2016.02); *A61B 2017/3409* (2013.01)

(56) References Cited

U.S. PATENT DOCUMENTS

| | | | | |
|---|---|---|---|---|
| 8,684,948 | B2 | 4/2014 | Nakata | |
| 8,825,135 | B2 | 9/2014 | Okada | |
| 2006/0173377 | A1 | 8/2006 | McCullough | |
| 2009/0112084 | A1* | 4/2009 | Piferi | A61B 5/055 600/421 |
| 2009/0171184 | A1 | 7/2009 | Jenkins | |
| 2011/0087132 | A1 | 4/2011 | Defreitas | |
| 2012/0004572 | A1 | 1/2012 | Krueger | |
| 2012/0172722 | A1* | 7/2012 | Chinowsky | A61B 17/282 600/439 |
| 2013/0131597 | A1* | 5/2013 | Blaivas | A61M 25/0113 604/173 |
| 2014/0094825 | A1 | 4/2014 | Flaherty | |

FOREIGN PATENT DOCUMENTS

| | | | |
|---|---|---|---|
| DE | 202009000119 | | 4/2009 |
| EP | 2485651 | | 8/2012 |
| JP | H0850531 | A | 2/1996 |
| JP | 2010253162 | A | 11/2010 |
| WO | WO2008153975 | A3 | 12/2008 |
| WO | 2012088535 | | 6/2012 |

* cited by examiner

USER INTERFACE FOR A BIOPSY UNIT

CROSS REFERENCE TO RELATED APPLICATIONS

This application is the U.S. National Phase application under 35 U.S.C. § 371 of International Application No. PCT/IB2014/062732, filed Jun. 30, 2014, published as WO 2015/008182 on Jan. 22, 2015, which claims the benefit of European Patent Application Number 13306039.2 filed Jul. 19, 2013. These applications are hereby incorporated by reference herein.

FIELD OF THE INVENTION

The present invention relates to operating a biopsy unit, and relates in particular to a control device for controlling a biopsy unit, to a biopsy system, and to a method for controlling a biopsy unit.

BACKGROUND OF THE INVENTION

Biopsy is used in relation with breast examinations, and in particular with mammography interventions. For mammography breast biopsy procedures, a biopsy needle is controlled by a user, for example via control buttons, to adjust the needle coordinates. For example, control buttons are provided for three axes of a Cartesian coordinate system. However, it has been shown that mammography breast biopsy procedures, for example, are stressful situations. Further, an increasing use of inclined needle positions exists, for example in combination with X-ray imaging systems that lead to certain space restrictions. Thus, the user is faced with a more complex situation with regards to the operation of the biopsy system.

SUMMARY OF THE INVENTION

There may thus be a need to provide an enhanced and facilitated way of controlling a biopsy unit.

The object of the present invention is solved by the subject-matter of the independent claims, wherein further embodiments are incorporated in the dependent claims. It should be noted that the following described aspects of the invention apply also for the control device for controlling a biopsy unit, the biopsy system, and the method for controlling a biopsy unit.

According to the present invention, a control device is provided for controlling a biopsy unit. The control device comprises a support structure with a housing and a user interface unit with a plurality of control elements. The control elements are configured to control the movement of a biopsy needle device along at least three moving direction lines. At least two of the moving direction lines are aligned to axes of a Cartesian coordinate system and one moving direction line is aligned to a needle axis direction of an elongated needle device of the biopsy unit, the needle axis direction being inclined to at least one of the axes of the Cartesian coordinate system. For each moving direction line, the housing is provided with a surface portion that is aligned with a respective one of the moving direction lines. The control element for each moving direction line is arranged on the housing on a respective one of the surface portions. The control element for the movement along the needle axis direction is provided on an inclined surface portion that is aligned with the inclined needle axis direction.

As an advantage, an intuitive way of operating the control device for the biopsy unit is provided. Due to the provision of control elements relating to the needle direction, and thus not only to the Cartesian coordinate system, and by providing those needle direction control elements on an inclined surface portion aligned with the inclined needle axis direction, the user can easily operate the needle, for example applying a displacement of the needle in the needle direction, which is one of the commonly used movements the user wants to perform.

In an example, the axes of the Cartesian coordinate system are aligned to a patient support, e.g. a patient support table. For example, the table may be provided such that it can be inclined or angled for certain procedures. In another example, the Cartesian coordinate system is aligned to a breast support that may be provided adaptable in the angular position with respect to the patient. In a further example, the axes of the Cartesian coordinate system are aligned to the coordinate system of an X-ray system associated with the biopsy arrangement. In another example, where the patient support is aligned with the vertical and horizontal direction in an examination room, the axes of the Cartesian coordinate system are aligned to the vertical and horizontal direction in the examination room, and a needle direction is provided inclined to the vertical direction. In a further example, the axes of the Cartesian coordinate system are aligned to the vertical and horizontal direction in an examination room, and the needle direction is provided inclined to the vertical direction.

According to an example, the control device is configured as a spatially adapted user interface. The control elements are arranged in the same direction as the needle will move when pressing on the control elements.

According to an example, the inclined surface portion is provided with an adaptable degree of inclination that is configured to be adapted to a change of the needle direction.

For example, the needle direction, or the needle inclination, is adjustable. By also adapting the inclination of the surface portion, an optimized way of an intuitive user interface is provided.

According to the present invention, also a biopsy system is provided, comprising a biopsy unit and a control device. The biopsy unit comprises an inclined elongated needle device and a movement arrangement for moving the needle device along at least three moving direction lines. At least two of the moving direction lines are aligned to axes of a Cartesian coordinate system of the biopsy system, and one moving direction line is aligned to the needle direction that is inclined to at least one of the axes of the Cartesian coordinate system. The control device is a control device according to one of the above-mentioned examples.

The elongated needle device is provided as a biopsy needle. The needle direction is provided inclined to at least one of the axes of the Cartesian coordinate system.

According to an example, the control device is mounted in a fixed relation with the biopsy unit.

For example, the control device is arranged remote of the biopsy unit. In an alternative example, the control device is arranged on a separate support in the vicinity of the biopsy unit.

According to a further example, an adjustable patient support is provided, and the Cartesian coordinate system is aligned with the patient support. In an operation position, the inclined surface portion is arranged with an inclined angle to the patient support.

According to an example, the biopsy unit comprises a stand support, and the control device is fixedly mounted to the stand support.

According to a further example, the biopsy unit comprises an X-ray imaging arrangement.

According to an example, the biopsy system is a mammography system and the object support is a breast support with a breast holding arrangement. A source or detector of the X-ray imaging system is arranged above the breast support. The needle device of the biopsy unit is arranged in a displaced manner above the breast support. In an example, the breast holding arrangement comprises two adjustable breast paddles.

According to the present invention, also a method for controlling a biopsy unit with an inclined needle direction is provided. The method comprises the following steps:

a) Providing control elements configured to control the movement of a biopsy needle device along at least three moving direction lines, wherein at least two of the moving direction lines are aligned to axes of a Cartesian coordinate system and one moving direction line is aligned to a needle axis direction of an elongated needle device of the biopsy unit, the needle axis direction being inclined to at least one of the axes of the Cartesian coordinate system. For each moving direction line, the housing is provided with a surface portion that is aligned with a respective one of the moving direction lines. The control element for each moving direction line is arranged on the housing on a respective one of the surface portions. The control element for the movement along the needle axis direction is provided on an inclined surface portion that is aligned with the inclined needle axis direction.

b) Activating at least one of the control elements for movement along the respective movement direction line.

c) Moving an inclined elongated needle device by a movement arrangement in at least one of three moving directions. At least two of the moving directions are aligned to axes of a Cartesian coordinate system of the biopsy system, and one moving direction is aligned to the needle direction that is inclined to at least one of the axes of the Cartesian coordinate system.

According to an aspect of the invention, besides control elements relating to movement along axes of a coordinate system, an additional, i.e. separate control is provided relating to movement in the needle's direction. To facilitate the transfer of the imaginary needed movement along the needle's axis to the actual activation of respective control elements by a user, the respective control elements relating to the needle direction, are provided on a surface portion that is associated with the inclination, or angular position of the biopsy needle itself. Thus, the user can easily imagine that the respective control elements do not need to be (mentally) transferred in a coordinate system, but can be activated directly and in a very intuitive manner. The geometrical setup of the buttons makes it easy and safe for the user to control the unit, even, for example, from the gantry. The buttons are placed in a way that an inclined vertical needle can be intuitively controlled in all directions, namely for example x-, y-, z-, and the needle elongation direction. Thus, the workflow is improved due to the reduction of the attention and distraction that is required from the user. For example, stereotactic breast biopsy systems are provided that make use of a straight vertical and lateral needle approach. During the biopsy procedure, the user can fine-adjust the needle coordinates by activating the respective buttons on the control unit. The control unit, i.e. the control device, is provided as implemented in the needle unit in one example. In another example, the control unit is a handheld, loose control unit. For example, the control device can be used for mammography systems where tomosynthesis imaging is used. The biopsy system can thus easily be integrated despite the tomosynthesis imaging setup. For example, such imaging setup cannot have a straight vertical needle, since the needle holster and the needle itself will give a shape feedback during the tomoscan.

These and other aspects of the present invention will become apparent from and be elucidated with reference to the embodiments described hereinafter.

BRIEF DESCRIPTION OF THE DRAWINGS

Exemplary embodiments of the invention will be described in the following with reference to the following drawings.

DETAILED DESCRIPTION OF EMBODIMENTS

Figure 1:
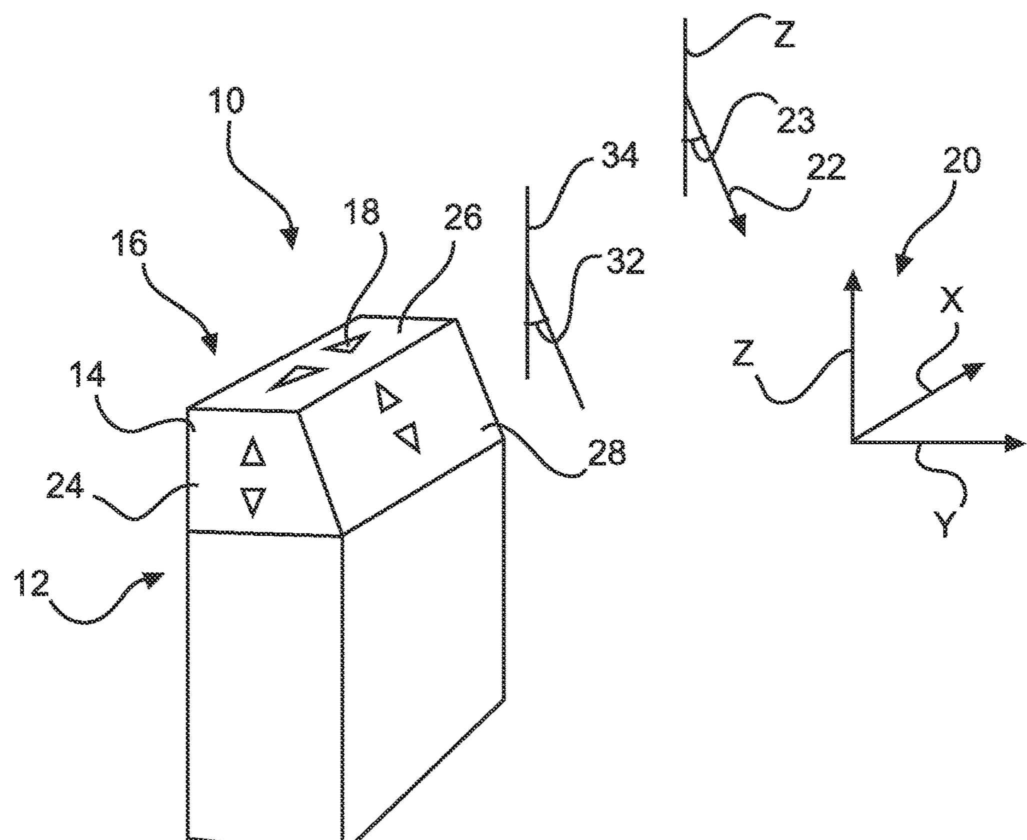
FIG. 1 schematically shows a perspective view of an example of a control device.

FIG. 1 shows a control device 10 for controlling a biopsy unit (not further shown). The control device 10 comprises a support structure 12 with a housing 14. Further, a user interface unit 16 with a plurality of control elements 18 is provided. The control elements 18 are configured to control the movement of a biopsy needle device along at least three moving direction lines. At least two of the moving direction lines are aligned to axes of a Cartesian coordinate system 20, as indicated in FIG. 1. One moving direction line is aligned to a needle axis direction 22 of an elongated needle device of the biopsy unit. The needle axis direction is inclined to at least one of the axes of the Cartesian coordinate system.

The term "biopsy needle device" relates to biopsy needles or other interventional equipment.

For example, the Cartesian coordinate system 20 may comprise a first z-axis, a second x-axis, and a third y-axis. As indicated by angle symbol 23, the needle axis direction 22 is provided with an inclination angle, i.e. the angle 23, to the z-axis.

For each moving direction line, the housing is provided with a surface portion that is aligned with a respective one of the moving direction lines. For example, a vertical surface portion 24, a horizontal surface portion 26, and an inclined surface portion 28 are provided. The inclination of the inclined surface portion 28 is indicated with a first line 30 parallel to the surface portion 28, having an inclination angle 32 with a vertical line 34. The control element for a vertical movement is provided on the vertical surface portion 24. The control element for at least one horizontal movement is provided on the horizontal surface portion 26. The control element for an inclined movement, i.e. along the needle direction, is provided on the inclined surface portion 28.

The terms "vertical movement", "horizontal movement", and "inclined movement" relate to movement in the vertical, horizontal, and inclined direction, respectively, i.e. to the above-described moving direction line or movement orientation in the vertical, horizontal, and inclined plane, respectively. In case of an association of a Cartesian coordinate system with a patient support that is adjustable, the terms “vertical”, “horizontal”, and “inclined” relate to the respective axes of the patient support with varying spatial orientation of the table.

The term “moving direction line” relates to a linear movement along a line of movement, wherein the linear movement is controllable and may occur in both directions. The “moving direction line” is also referred to as a moving orientation, wherein the moving orientation comprises two opposite moving directions. The “moving direction line” is also referred to as “moving direction”, wherein the term “direction” refers to two opposite directions, i.e. back and forth, along a movement path.

The “needle axis direction” is also referred to as needle orientation with two opposite directions, or also as needle orientation.

The term “inclined” relates to a deviation of the needle direction from the Cartesian axes of at least 5°, for example a deviation of 10°, or more.

The term “aligned” relates to the same orientation of the moving direction and of the respective surface portion. For example, aligned comprises a parallel arrangement. In another example, the term “inclined” also comprises a deviation from the parallel alignment, for example a deviation of +/−5° or +/−10°.

The term “spatially adapted” relates to the arrangement of the control elements on surfaces that are provided in a similar spatial position, i.e. in a similar orientation (with respect to the operational space where the biopsy unit is provided), as the controllable movement possibilities of the biopsy device, e.g. the biopsy needle.

The term “user interface” relates to the provided control function of the biopsy unit, i.e. the interaction direction user-machine, as well as to the direct feedback function or information function provided by the control device itself, i.e. the interaction direction machine-user.

Figure 2:
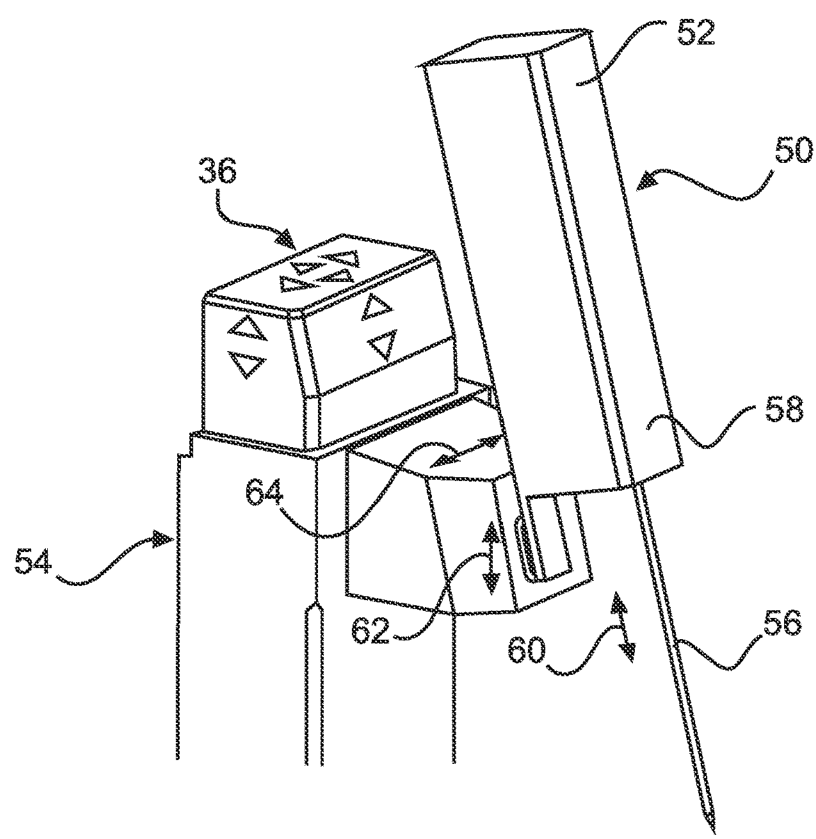
FIG. 2 shows a further example of a control device in relation with a biopsy needle.

In an example, a control element for two horizontal moving directions perpendicular to each other, indicated with reference sign 36 in FIG. 2, is provided on the horizontal surface portion 26.

In another example, a control element for controlling the movement of the biopsy needle in a respective direction along the moving direction line is provided as two buttons, with one button for each direction, as schematically shown in FIGS. 1 and 2.

In a further example (not shown), a button with two activation surface portions is provided, and the buttons are provided for controlling the movement of the biopsy needle in a respective direction along the moving direction line.

For example, the buttons, or activation surface portions are provided in the shape of an arrow indicating the respective direction.

As indicated above, the control element for each moving direction line is arranged on the housing on a respective one of the surface portions. The control element for the movement along the needle axis direction is provided on the inclined surface portion 28 that is aligned with the inclined needle axis direction.

The control device 10 is configured as a spatially adapted user interface, wherein the control elements are arranged in the same direction as the needle will move when pressing on the control elements.

FIG. 2 shows a biopsy system 50 with a biopsy unit 52 and a control device 54. The control device 54 is a control device 10 according to one of the above-mentioned examples. The biopsy unit 52 comprises an inclined elongated needle direction 56 and a movement arrangement 58 for moving the needle device along at least three moving direction lines, i.e. along a first direction aligned with the needle direction, as indicated with first double arrow 60. Further, also a vertical movement is provided, as indicated with second double arrow 62, as well as a horizontal movement, indicated with a second horizontal double arrow, i.e. a third double arrow 64. At least two of the moving direction lines are aligned to axes of a Cartesian coordinate system of the biopsy system, and one moving direction line is aligned to the needle direction that is inclined to at least one of the axes of the Cartesian coordinate system.

According to the example shown in FIG. 2, the control device is mounted in a fixed relation with the biopsy unit, for example attached with each other, as shown in FIG. 2. However, in other examples, the control device is mounted fixed, but with a distance to the biopsy unit 52.

In another example, the control device is arranged remote of the biopsy unit. In an alternative example, the control device is arranged on a separate support in the vicinity of the biopsy unit.

According to an example, the support structure 12 is associatable with an adjustable patient support. The Cartesian coordinate system is aligned with the patient support, and in an operation position, the inclined surface portion is arranged with an inclined angle to the patient support.

Figure 3:
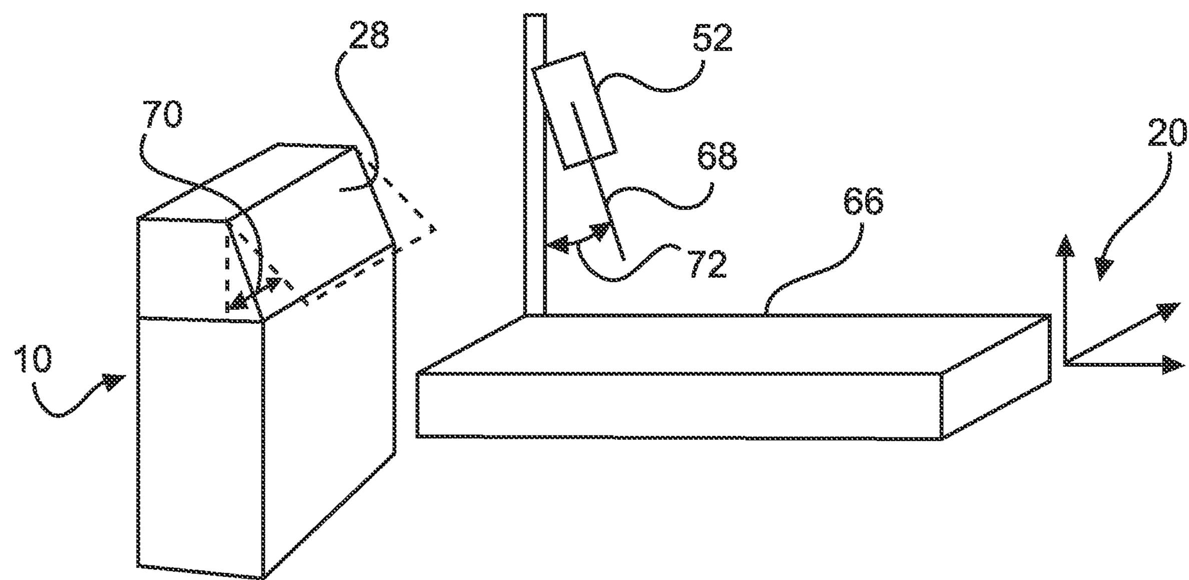
FIG. 3 shows a schematic setup of an example of a biopsy system.

For example, as shown in FIG. 3, an adjustable patient support 66 is provided, for example a patient table. The Cartesian coordinate system 20, shown in the vicinity of the patient table, is aligned with the patient support, and, in an operation position, the inclined surface portion is arranged with an inclined angle to the patient support, as indicated by the inclination of the inclined surface portion 28. Further, also the inclined needle direction is shown, as indicated with reference numeral 68.

According to a further example, shown as an option in FIG. 3, the inclined surface portion 28 is provided with an adaptable degree of inclination, as indicated with first pivoting double arrow 70. The adaptable degree of inclination is configured to be adapted to a change of the needle direction, which is indicated with a second pivoting double arrow 72.

Figure 4:
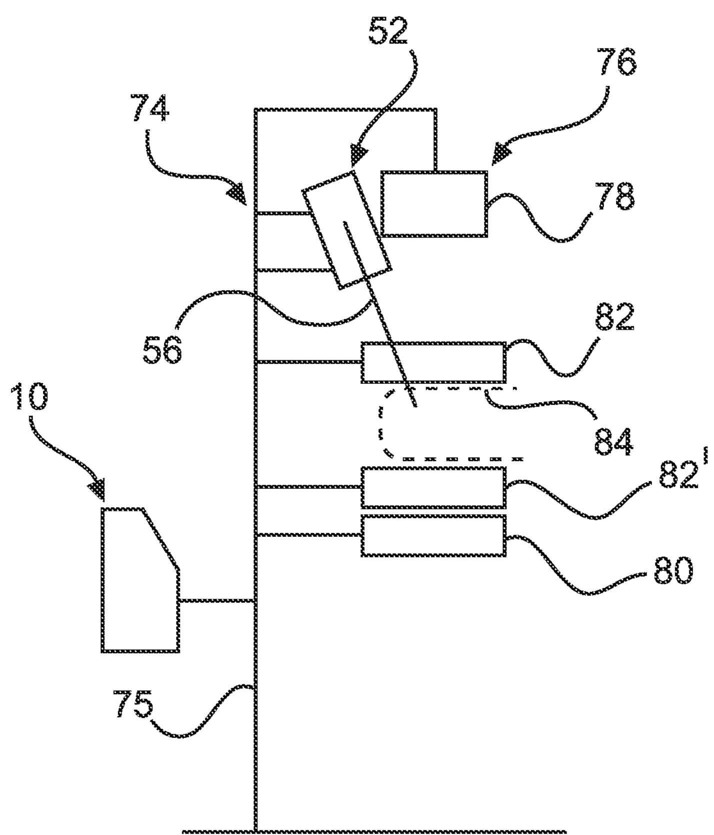
FIG. 4 shows a further example of a biopsy system with a stand support for mammography biopsy interventions.
Figure 5:
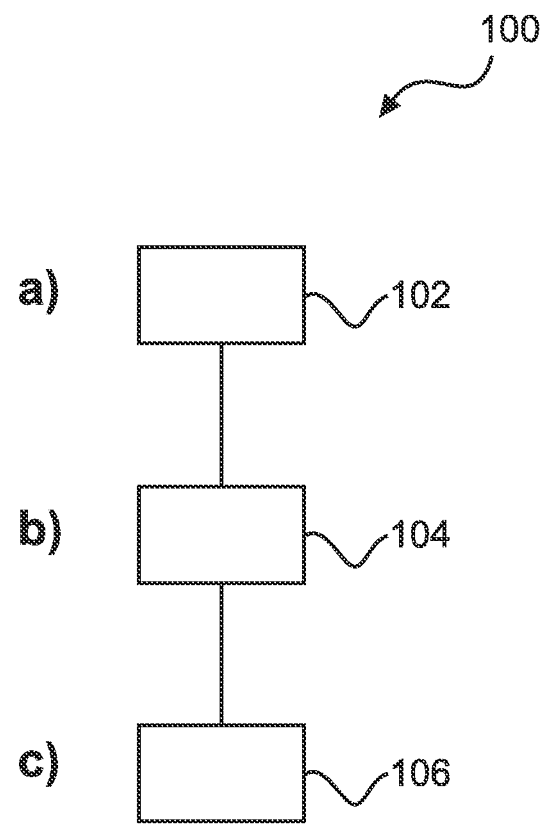
FIG. 5 shows basic steps of an example of a method for controlling a biopsy unit.

As shown in FIG. 4, a further example is provided, wherein the biopsy unit 52 comprises a stand support 74. The control device 10 is fixedly mounted to the stand support. The stand support is indicated with an upright structure 75. For example, the biopsy unit comprises an X-ray imaging arrangement 76, for example with an X-ray source 78, and an X-ray detector 80. For example, the system is a mammography system and the object support is a breast support with a breast holding arrangement 82. A dotted line 84 indicates a breast arranged between two breast paddles. A source or detector of the X-ray imaging system is arranged above the breast support, and the needle device of the biopsy unit 52 is arranged in a displaced manner above the breast support, and for example moved to the left in FIG. 4.

The term “displaced manner above” relates to the position that is a) above the breast support, i.e. in vertical direction higher than the breast support, and b) displaced to the side, for example adjacent to the source or detector of the X-ray imaging system.

In an example, the breast holding arrangement comprises two adjustable breast paddles, as already mentioned.

According to the present invention, also a method 100 for controlling a biopsy unit with an inclined needle direction is provided. The method 100 comprises the following steps: In a first provision step 102, control elements are provided that are configured to control the movement of a biopsy needle device along at least three moving direction lines. At least two of the moving direction lines are aligned to axes of a Cartesian coordinate system and one moving direction line is aligned to a needle axis direction of an elongated needle device of the biopsy unit. The needle axis direction is inclined to at least one of the axes of the Cartesian coordinate system. For each moving direction line, the housing is provided with a surface portion that is aligned with a respective one of the moving direction lines. The control element for each moving direction line is arranged on the housing on a respective one of the surface portions. The control element for the movement along the needle axis direction is provided on an inclined surface portion that is aligned with the inclined needle axis direction. In a further activation step 104, at least one of the control elements for a movement along the respective movement direction line is activated. In a third movement step 106, an inclined elongated needle device is moved by a movement arrangement in at least one of three moving directions. At least two of the moving directions are aligned to axes of a Cartesian coordinate system of the biopsy system, and one moving direction is aligned to the needle direction that is inclined to at least one of the axes of the Cartesian coordinate system.

The first, i.e. provision step 102 is also referred to as step a), the second step, i.e. activation step 104 is also referred to as step b), and the third, i.e. moving step 106 is also referred to as step c).

It has to be noted that embodiments of the invention are described with reference to different subject matters. In particular, some embodiments are described with reference to method type claims whereas other embodiments are described with reference to the device type claims. However, a person skilled in the art will gather from the above and the following description that, unless otherwise notified, in addition to any combination of features belonging to one type of subject matter also any combination between features relating to different subject matters is considered to be disclosed with this application. However, all features can be combined providing synergetic effects that are more than the simple summation of the features.

While the invention has been illustrated and described in detail in the drawings and foregoing description, such illustration and description are to be considered illustrative or exemplary and not restrictive. The invention is not limited to the disclosed embodiments. Other variations to the disclosed embodiments can be understood and effected by those skilled in the art in practicing a claimed invention, from a study of the drawings, the disclosure, and the dependent claims.

In the claims, the word “comprising” does not exclude other elements or steps, and the indefinite article “a” or “an” does not exclude a plurality. A single processor or other unit may fulfil the functions of several items re-cited in the claims. The mere fact that certain measures are re-cited in mutually different dependent claims does not indicate that a combination of these measures cannot be used to advantage. Any reference signs in the claims should not be construed as limiting the scope.

The invention claimed is:

1. A control device for controlling a biopsy unit, the control device comprising:

a support structure including a housing; and a user interface unit including a plurality of direction controls, wherein the plurality of direction controls includes first, second, and third direction controls that are configured to control moving of a biopsy needle device along first, second, and third moving direction lines of at least three moving direction lines, respectively;

wherein the first and the second moving direction lines are substantially parallel with two axes of a Cartesian coordinate system, respectively, and the third moving direction line is substantially parallel with a needle axis direction of the biopsy needle device of the biopsy unit, the needle axis direction being inclined to at least one of the axes of the Cartesian coordinate system;

wherein the housing includes a plurality of surface portions, the plurality of surface portions including:

a first surface portion substantially parallel with the first moving direction line, wherein the first direction control is arranged on the first surface portion; and an inclined surface portion that is inclined to the first surface portion, wherein the inclined surface portion is substantially parallel with the third moving direction line, and wherein the third direction control for the moving along the needle axis direction is arranged on the inclined surface portion, and is spaced apart from the first surface portion to which the inclined surface portion is inclined and on which the first direction control is arranged; and wherein the first, the second, and the third direction controls are in direct correspondence to the first, the second, and the third moving direction lines, respectively.

2. The control device according to claim 1, wherein the control device is configured as a spatially adapted user interface, and wherein the direction controls are arranged in the same direction as the movement of the biopsy needle device when activating the direction controls.

3. The control device according to claim 1, wherein the support structure is associated with an adjustable patient support; wherein the Cartesian coordinate system is substantially parallel with the patient support; and wherein in an operation position, the inclined surface portion is arranged with an inclined angle to the patient support.

4. The control device according to claim 1, wherein the plurality of surface portions of the housing include a second surface portion, wherein one surface portion of the first and the second surface portions is a vertical surface portion, and one direction control of the first and the second direction controls is for a vertical movement and is arranged on the vertical surface portion;

wherein the other surface portion of the first and the second surface portions is a horizontal surface portion, and the other direction control of the first and the second direction controls is for at least one horizontal movement and is arranged on the horizontal surface portion; and wherein the inclined surface portion is inclined to the vertical direction.

5. The control device according to claim 1, wherein the inclined surface portion is provided with an adaptable degree of inclination that is configured to follow a change in direction of the biopsy needle device.

6. A biopsy system, comprising:

a biopsy unit including a biopsy needle device that is moved along at least three moving direction lines; and a control device for controlling the biopsy unit, the control device comprising:

a support structure including a housing; and a user interface unit including a plurality of direction controls, wherein the plurality of direction controls includes first, second, and third direction controls that are configured to control moving of the biopsy needle device along first, second, and third moving direction lines of the at least three moving direction lines, respectively;

wherein the first and the second moving direction lines are substantially parallel with two axes of a Cartesian coordinate system, respectively, and the third moving direction line is substantially parallel with a needle axis direction of the biopsy needle device of the biopsy unit, the needle axis direction being inclined to at least one of the axes of the Cartesian coordinate system;

wherein the housing includes a plurality of surface portions, the plurality of surface portions including:

a first surface portion substantially parallel with the first moving direction line, wherein the first direction control is arranged on the first surface portion; and an inclined surface portion that is inclined to the first surface portion, wherein the inclined surface portion is substantially parallel with the third moving direction line, and wherein the third direction control for the moving along the needle axis direction is arranged on the inclined surface portion, and is spaced apart from the first surface portion to which the inclined surface portion is inclined and on which the first direction control is arranged, wherein the first, the second, and the third direction controls are in direct correspondence to the first, the second, and the third moving direction lines, respectively.

7. The system according to claim 6, wherein the control device is mounted in a fixed relation with the biopsy unit.

8. The system according to claim 6, wherein an adjustable patient support is provided; wherein the Cartesian coordinate system is substantially parallel with the adjustable patient support; and wherein in an operation position, the inclined surface portion is arranged with an inclined angle to the adjustable patient support.

9. The system according to claim 6, wherein the biopsy unit comprises a stand support; and wherein the control device is fixedly mounted to the stand support.

10. The system according to claim 6, wherein the biopsy unit comprises an X-ray imaging system.

11. The system according to claim 10, wherein the biopsy system is a mammography system, and the object support is a breast support with a breast holding arrangement;

wherein a source or detector of the X-ray imaging system is arranged above the breast support; and wherein the biopsy needle device is arranged above the breast support.

12. A method for controlling a biopsy unit with an inclined needle axis direction, comprising:

providing a plurality of direction controls wherein the plurality of direction controls includes first, second, and third direction controls that are configured to control moving of a biopsy needle device along first, second, and third moving direction lines of at least three moving direction lines, respectively; wherein the first and the second moving direction lines are substantially parallel with two axes of a Cartesian coordinate system, respectively, and the third moving direction line is substantially parallel with the inclined needle axis direction of the biopsy needle device of the biopsy unit, the inclined needle axis direction being inclined to at least one of the axes of the Cartesian coordinate system;

wherein a housing includes a plurality of surface portions, the plurality of surface portions including:

a first surface portion substantially parallel with the first moving direction line wherein the first direction control is arranged on the first surface portion; and an inclined surface portion that is inclined to the first surface portion, wherein the inclined surface portion is substantially parallel with the third moving direction line, and wherein the third direction control for the moving along the needle axis direction is arranged on the inclined surface portion, and is spaced apart from the first surface portion to which the inclined surface portion is inclined and on which the first direction control is arranged, wherein the first, the second, and the third direction controls are in direct correspondence to the first, the second, and the third moving direction lines, activating at least one of the direction controls for the movement along the respective movement direction line; and moving the biopsy needle device in one or more of the first, the second, and the third moving directions.

* * * * *